United States Patent
Thanner

(10) Patent No.: US 7,513,157 B2
(45) Date of Patent: Apr. 7, 2009

(54) METHOD AND DEVICE FOR DETERMINING THE REDOX STATE OF A REACTION SURFACE COATED WITH A CATALYST MATERIAL

(75) Inventor: Herbert Thanner, Graz (AT)

(73) Assignee: AVL List GmbH, Graz (AT)

(*) Notice: Subject to any disclaimer, the term of this patent is extended or adjusted under 35 U.S.C. 154(b) by 513 days.

(21) Appl. No.: 10/549,632

(22) PCT Filed: Mar. 18, 2004

(86) PCT No.: PCT/AT2004/000100

§ 371 (c)(1),
(2), (4) Date: Sep. 20, 2005

(87) PCT Pub. No.: WO2004/083838

PCT Pub. Date: Sep. 30, 2004

(65) Prior Publication Data

US 2006/0174705 A1 Aug. 10, 2006

(30) Foreign Application Priority Data

Mar. 20, 2003 (AT) .............................. A 449/2003

(51) Int. Cl.
*G01N 29/04* (2006.01)
(52) U.S. Cl. .................... 73/579; 73/24.01; 73/649; 73/657
(58) Field of Classification Search ............... 73/24.06, 73/24.04, 31.05, 31.06, 23.21, 61.79, 64.53, 73/579, 24.01, 649, 657; 423/210, 219
See application file for complete search history.

(56) References Cited

U.S. PATENT DOCUMENTS

| 3,879,992 | A | | 4/1975 | Bartera |
| 5,827,947 | A | | 10/1998 | Miller et al. |
| 5,958,787 | A | * | 9/1999 | Schonfeld et al. ........... 436/116 |
| 6,083,637 | A | | 7/2000 | Walz et al. |

(Continued)

FOREIGN PATENT DOCUMENTS

EP 1143241 10/2001

(Continued)

*Primary Examiner*—Hezron Williams
*Assistant Examiner*—J M Saint Surin
(74) *Attorney, Agent, or Firm*—Dykema Gossett PLLC

(57) ABSTRACT

The invention relates to a method and device for determining the redox state of an anode (11), which is coated with a catalyst material or consisting thereof, associated with a high temperature fuel cell (10) or a reaction surface (16) of a reformer (13). According to the invention, at least one first resonator (3) of a piezoelectric sensor device (1) is arranged in the anode gas flow (5) of the high temperature fuel cell or in the gas flow of the reformer (13). The first resonator (3) is provided with a coating (4) which is oxidizable or reducible in the gas flow. The device also comprises a device (8) for measuring at least one modification of the resonance behaviour of the first resonator (3). The detected measuring value acts as an indicator of the redox state of the anode (11) of the high temperature fuel cell (10) or reaction surface (16) of the reformer (13).

18 Claims, 1 Drawing Sheet

U.S. PATENT DOCUMENTS

| | | | |
|---|---|---|---|
| 6,155,099 A * | 12/2000 | Kobayashi et al. | 73/31.05 |
| 6,222,366 B1 | 4/2001 | Dilger | |
| 6,455,181 B1 | 9/2002 | Hallum | |
| 7,201,041 B2 * | 4/2007 | Itoh et al. | 73/54.41 |
| 7,329,536 B2 * | 2/2008 | Zeng et al. | 435/287.2 |

FOREIGN PATENT DOCUMENTS

| | | |
|---|---|---|
| GB | 1049742 | 11/1966 |
| WO | 00/66266 | 11/2000 |

* cited by examiner

METHOD AND DEVICE FOR DETERMINING THE REDOX STATE OF A REACTION SURFACE COATED WITH A CATALYST MATERIAL

BACKGROUND OF THE INVENTION

1. Field of the Invention

The invention relates to a method and device for determining the redox state of the anode of a high-temperature fuel cell, which is coated with or made from catalyst material, or of the reaction surface of a reformer, and further to a piezoelectric sensor device for determining the redox state of an oxidizable/reducible coating.

2. The Prior Art

High-temperature fuel cells, such as e.g. the solid oxide fuel cell or the molten carbonate fuel cell, must be supplied with gases at the electrodes during operation, i.e. combustion gas ($H_2$, CO or $CH_4$) at the anode and oxidizing gas ($O_2$ or air) at the cathode. The gas spaces must be sealed against each other. Insufficient sealing results in a reduction of the cell voltage and usually leads to degradation and failure of the fuel cell.

In addition, if oxygen enters an $H_2$-enriched anode space at temperatures below 600° C., a highly explosive mixture will result.

Nickel (Ni) or nickel-cermet may be used as catalyst material at the anode, but this will form nickel oxide (NiO) in contact with an atmosphere containing oxygen, and its catalytic activity will deteriorate. For this reason starting the operation of a high-temperature fuel cell with Ni or Ni-cermet as anode material requires a so-called reduction phase during which the anode space is initially flushed with nitrogen and is then subjected to the combustion gas (e.g. hydrogen), which acts as reducing agent and whose concentration is increased in a stepwise manner. During this reduction phase NiO is reduced to metallic Ni. Conversely, oxidation of the anode material cannot be avoided on certain occasions, e.g. during maintenance activities. Reduction and oxidation of the anode is referred to as the "redox cycle".

It is known practice to determine such redox cycles, or the redox state, of Ni/YsZ-cermet anodes (YsZ=yttrium doped zirkonium) via their polarisation state, for instance by impedance spectroscopy. This method is used primarily in the development of fuel cells, but reliable inferences regarding the catalytic activity of the anode are only possible in single cell experiments. The method is not suitable for continuous monitoring of high-temperature fuel cells during operation.

From "Kinetics of Oxidation and Reduction of Ni/YsZ Cermets", 5$^{th}$ European Solid Oxide Fuel Cell Forum, Vol. 1 (2002), pp. 467-474, authored by Daniel Fouquet, Axel C. Müller, André Weber, and Ellen Ivers-Tiffée, there have become known findings concerning the kinetics of the reduction and oxidation of NiO/Ni powder and NiO/Ni-YsZ cermets, obtained with the use of TGA measurements (Thermo Gravimetric Analysis). Measurements of this kind cannot be used for the continuous monitoring of high-temperature fuel cells, however.

Reformers, e.g. vapour reformers for the generation of hydrogen-rich combustion gas for fuel cells, have reaction surfaces coated with catalyst materials, at which a combustion gas containing $H_2$ and CO is obtained, for instance from the primary media natural gas and water vapour. Reformers working with methanol as a primary medium are also used to generate a hydrogen-rich combustion gas according to the equation $$CH_3OH+H_2O+heat \rightarrow 3H_2+CO_2$$

Different redox layers, e.g. Ni/NiO or nickel-cermet, are used as catalyst materials. Efficiency and operational safety of the reformer depend on the state of the reaction surface.

From U.S. Pat. No. 6,455,181 B1 a fuel cell assembly is known which has a sensor with a membrane electrode, whose one side is connected with the gas feed of the fuel cell and whose other side is connected with the exhaust of the fuel cell, the two sides having different coatings. The different composition of the gas on the two sides of the membrane, for instance a difference in hydrogen ion concentration, is converted into an electric signal, which can be used to control the gas flow of the fuel cell. Thus differences in the gas concentration at the inlet and the outlet of the fuel cell are measured, but the device cannot be used for determination of the redox state of the anode of a high-temperature fuel cell or the redox state of the reaction surface of a reformer.

It is the object of the present invention to propose a method and device as well as a sensor arrangement for the monitoring of the redox state of the anode of a high-temperature fuel cell or of the catalytic reaction surface of a reformer, which may be used during normal operation and which should furthermore ensure optimised and safe operation of the fuel cell or fuel cell assembly including the reformer, by controlling or adjusting at least one operational parameter.

SUMMARY OF THE INVENTION

The invention achieves its aim by providing that at least a first resonator of a piezoelectric sensor device is brought into contact with the anode gas flow containing $H_2$ and/or CO and/or $CH_4$, of the high-temperature fuel cell, the surface of the first resonator being furnished with a coating which can be oxidized/reduced in the anode gas flow, and that at least one change in the resonance properties, preferably the resonance frequency, of the first resonator is measured and the redox state of the anode of the high-temperature fuel cell is inferred from this measurement.

For monitoring the reaction surface of a reformer the invention proposes that at least one first resonator of a piezoelectric sensor device be brought into contact with the gas flow of the reformer containing $H_2$ and/or CO and/or $CH_4$, the surface of the first resonator being provided with a coating that can be oxidized/reduced in the gas flow, and that at least one change in the resonance properties, preferably the resonance frequency, of the first resonator be measured and the redox state of the reaction surface of the reformer be inferred from this measurement.

A device according to the invention for implementing the method is characterised in that a first resonator of a piezoelectric sensor device is positioned in the anode gas flow of the high-temperature fuel cell or in the gas flow of the reformer, this first resonator being coated with an oxidizable/reducible layer, and that there is provided a unit for measuring at least one change of the resonance properties of the first resonator, the measured value being a measure for the redox state of the high-temperature fuel cell or a measure for the redox state of the reaction surface of the reformer.

In an advantageous variant of the invention the oxidizable/reducible coating of the first resonator is made from material identical with the catalyst material of the anode of the high-temperature fuel cell or the catalyst material of the reaction surface of the reformer.

Free standard-formation-energy of oxides, which depends on temperature and partial pressure of oxygen, may be read off the so-called Ellingham diagram for oxides, which is of importance especially in the extraction of metals from oxides. Examples of oxidizable/reducible coatings of the first resonator (for gases containing CO and/or $H_2$ or $CH_4$) include Cu/CuO, Ni/NiO, Pb/PbO, Co/CoO, Ag/AgO, Pd/PdO and nickel-cermet).

For difference measurements the invention proposes that at least one second resonator of the piezoelectric sensor device be placed in the gas flow, this second resonator having a coating which is chemically stable in the gas flow. The frequency difference between the first and second resonator of the sensor device is used as a measure for the redox state of the oxidizable/reducible layer. Examples of chemically stable layers (for gases containing CO and/or $H_2$ or $CH_4$) are CaO, MgO, $Al_2O_3$, $TiO_2$, $SiO_2$, MnO, V/VO, Cr/CrO, and noble metals.

It is proposed by the invention that, depending on the measured change of resonance properties, preferably the change in resonance frequency, at least one operational parameter of the high-temperature fuel cell or the reformer be controlled or adjusted.

According to the invention further operational parameters may be obtained by measuring the resonance frequency or resonance resistance of one of the two resonators, preferably the resonator with the chemically stable coating, and by using the measured value as a measure for temperature or pressure in the gas flow. From the data on temperature, pressure and redox state obtained at the measurement location the redox state of the anode may be found using pressure and temperature data from the anode space of a fuel cell. The device of the invention permits for instance control of the combustion gas supply or of the composition of the combustion gas at the anode and/or temperature control during the start and/or stop phase.

A piezoelectric sensor device for determination of the redox state of an oxidizable/reducible coating according to the invention is characterised in that the oxidizable/reducible coating is applied to the surface of at least one first resonator of the sensor device, the resonator surface being flow-connected to the anode gas space of a high-temperature fuel cell or the gas space of a reformer. Preferentially, a chemically stable coating is applied to the surface of at least one second resonator of the sensor device, which coating does not show any redox behaviour in the gas flow of the high-temperature fuel cell or of the reformer. Both resonators may preferably be configured as BAW- or SAW-resonators.

In a preferred application the piezoelectric sensor according to the invention can be used to detect oxygen leaking into the anode space, in particular during the critical start-up phase (e.g. from the cathode space), whereupon a switch off or emergency shutdown procedure for the fuel cell assembly may be initiated.

The piezoelectric sensor device may be positioned on the inlet side or on the outlet side of the anode gas flow of the fuel cell. During normal operation of the fuel cell the gas composition at the outlet of the fuel cell (e.g. $CH_4$, $H_2$, CO, $CO_2$, $N_2$, and $H_2O$) is temperature- and load-dependent.

In a variant of the invention the piezoelectric sensor device may also be placed in the anode gas space of the high-temperature fuel cell or on the outlet side of the gas flow from the reformer.

The invention will now be explained in more detail using the enclosed schematic drawings as reference.

BRIEF DESCRIPTION OF THE PREFERRED EMBODIMENTS

DETAILED DESCRIPTION OF THE PREFERRED EMBODIMENTS

Figure 1:
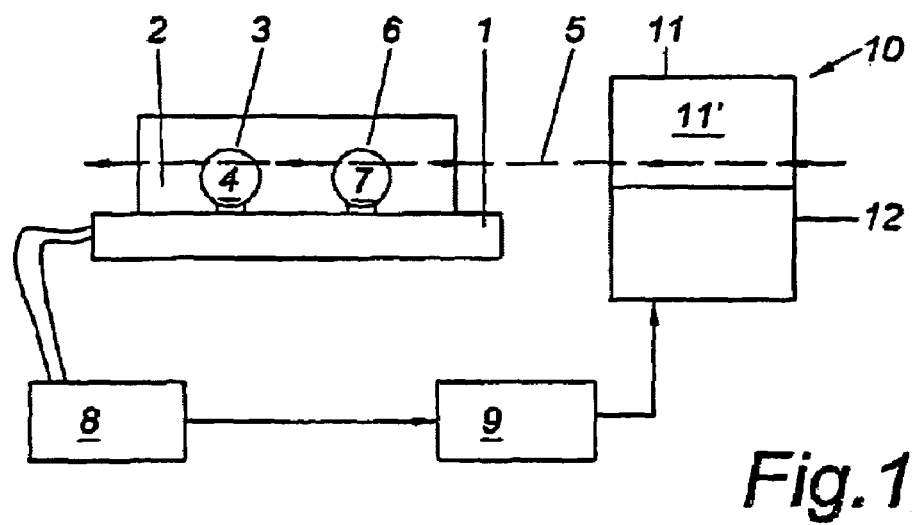
FIG. 1 is a schematic view of the device of the invention for determining the redox state of the anode of a high-temperature fuel cell with the piezoelectric sensor according to the invention.

FIG. 1 shows a device for determining the redox state of the anode 11, either coated with or consisting of a catalyst material, of a high-temperature fuel cell 10, where in the anode gas flow 5 containing $H_2$ and/or CO and/or $CH_4$ a piezoelectric sensor device 1 is located, whose first resonator 3 is furnished with a coating 4, which can be oxidized/reduced in the anode gas flow. The surface of the resonator is flow-connected to the anode gas space 11' and, in the example shown, placed on the outlet side of the high-temperature fuel cell 10. The cathode of the fuel cell 10 is referred to as 12.

The sensor device 1 has a second resonator 6, whose surface is provided with a chemically stable, inert coating 7, which does not exhibit any redox behaviour in the anode gas flow 5 of the high-temperature fuel cell 10. The second resonator 6 may for instance be coated with a noble metal or an inert oxide layer. The chemically stable coating 7 and the oxidizable/reducible coating 4 of resonators 3 and 6 may be applied onto two areas of a piezoelectric crystal element 2, as shown in FIG. 1. Both resonators will thus have the same material-dependent parameters, making signal evaluation substantially easier.

If SAW-resonators are used, excitation of the resonators and signal pick-up may be carried out by wireless methods.

If the first resonator 3 is designed as a BAW-resonator, its opposing surfaces may each be coated with the oxidizable/reducible coating 4, thereby achieving double signal intensity per mass.

It is furthermore possible to measure resonance frequency or resonance resistance by means of the resonator 6 with chemically stable coating 7, and to use the obtained value as a measure for temperature or pressure in the anode gas flow 5.

The device of FIG. 1 is provided with a unit 8 for measuring at least one change of the resonance properties (e.g. resonance frequency) of the resonators 3 and 6 of the piezoelectric sensor device 1, the obtained value yielding a measure for the redox state of the anode 11 of the high-temperature fuel cell 10. Via a control unit 9 diverse operational parameters of the high-temperature fuel cell 10 may be controlled.

Figure 2:
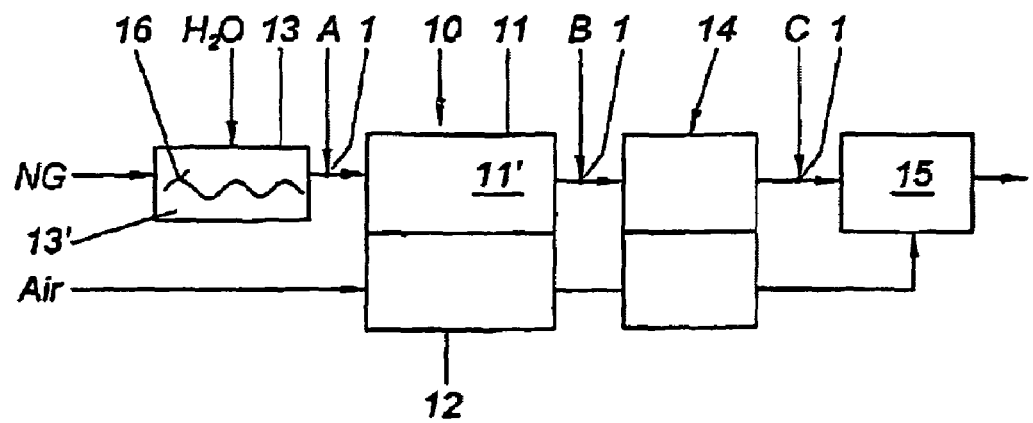
FIG. 2 is a variant of the device of FIG. 1 in a fuel cell assembly with a vapour reformer.

In, FIG. 2 a fuel cell assembly with a fuel cell 10 and a vapour reformer 13 running on natural gas is schematically shown. The piezoelectric sensor 1 described in FIG. 1 may be placed in the anode gas flow in front of the anode 11 of the fuel cell 10, respectively on the exit side of the gas flow from the reformer 13 (point A), and via the measurement data gathered it may provide information concerning the state of the anode 11 in the anode gas space 11' of the fuel cell 10, as well as the state of the reaction surface 16 in the gas space 13' of the reformer 13. The sensor device 1 could also be placed on the entry side of the reformer 13 (e.g. in a common feed line for natural gas and water vapour), or behind the anode 11 (point B), or also behind an optional heat exchanger 14 and in front of an afterburner 15 (point C).

The invention claimed is:

1. A Method for determining the redox state of an anode of a high-temperature fuel cell or a reaction surface of a reformer, which anode or reaction surface is in contact with a gas flow containing at least one of $H_2$, CO and $CH_4$ and is coated with or made from a catalyst material, comprising the steps of
   (a) bringing at least a first resonator of a piezoelectric sensor device into contact with said gas flow of said high-temperature fuel cell or said reformer, a surface of the first resonator having a coating which is oxidized or reduced in said gas flow,
   (b) measuring at least one change in a resonance property of the first resonator, and
   (c) inferring the redox state of the anode of said high-temperature fuel cell or the reaction surface of said reformer from a change of the resonance properties of the first resonator.

2. Method according to claim 1, wherein the resonance property is resonance frequency.

3. The method according to claim 1, including a step of controlling or adjusting an operational parameter of the high-temperature fuel cell depending on the measured change resonance property.

4. The method according to claim 1, comprising bringing a second resonator of the piezoelectric sensor device into contact with the gas flow containing at least one of $H_2$, CO and $CH_4$, said second resonator having a coating which is chemically stable, and wherein a frequency difference between the first and second resonator of the sensor device is used as a measure for the redox state of said anode or said reaction surface.

5. The method according to claim 4, comprising measuring a value of resonance resistance of one of the first and second resonators and the measured value is used as a measure for gas flow pressure.

6. The method according to claim 4, comprising measuring a value of resonance frequency of one of the first and second resonators and the measured value is used as a measure for gas flow temperature.

7. A device for determining the redox state of an anode of a high-temperature fuel cell or a reaction surface of a reformer, which anode or reaction surface is coated with or made from a catalyst material, comprising a first resonator of a piezoelectric sensor device which is positionable in a gas flow of said high-temperature fuel cell or said reformer, said first resonator having an oxidizable and reducible coating thereon, and a unit for measuring at least one change in a resonance property of said first resonator, the measured change being a measure for the redox state of the anode of said high-temperature fuel cell or of the reaction surface of said reformer.

8. The device according to claim 7, wherein the oxidizable and reducible coating of the first resonator is made from material identical with the catalyst material of the anode of the high-temperature fuel cell or the catalyst material of the reaction surface of the reformer.

9. The device according to claim 8, wherein the oxidizable and reducible coating of the first resonator is made from nickel-cermet, Ni/NiO, Cu/CuO, Pb/PbO, Co/CoO, Ag/AgO, or Pd/PdO.

10. The device according to claim 7, wherein the piezoelectric sensor device comprises at least one second resonator which is positionable in the gas flow of said fuel cell or said reformer, said second resonator having a coating which is chemically stable in said gas flow.

11. The device according to claim 10, wherein the chemically stable coating of the second resonator is a noble metal or an oxide layer.

12. The device according to claim 11, wherein the chemically stable coating is an oxide layer comprising at least one oxide of a group consisting of $SiO_2$, $TiO_2$, $Al_2O_3$, CaO, MgO, and MnO.

13. The device according to claim 7, wherein the piezoelectric sensor device is positioned on an outlet side of the anode gas flow of the high-temperature fuel cell.

14. The device according to claim 7, wherein the piezoelectric sensor device is placed in an anode gas space of the high-temperature fuel cell.

15. The device according to claim 7, wherein the piezoelectric sensor device is placed on the inlet or outlet side of the gas flow into or from the reformer.

16. The device according to claim 7, wherein the first and second resonators are configured as BAW- or SAW-resonators.

17. The device according to claim 7, wherein the first resonator is configured as a BAW-resonator with an oxidizable and reducible coatings on both opposite surfaces.

18. The device according to claim 7, wherein the chemically stable coating and the oxidizable and reducible coating are present on two areas of one piezoelectric crystal element.

* * * * *